(12) United States Patent
Bae et al.

(10) Patent No.: US 10,485,741 B2
(45) Date of Patent: Nov. 26, 2019

(54) COMPOSITION OF MATERIALS CONTAINING FLUORIDE VARNISH AND ANTIBACTERIAL AGENTS FOR PREVENTION AND TREATMENT OF DENTAL CARIES

(71) Applicant: WONKWANG UNIVERSITY CENTER FOR INDUSTRY-ACADEMY COOPERATION, Jeollabuk-do (KR)

(72) Inventors: Ji-Myung Bae, Daejeon (KR); Ju-Lee Son, Jeollabuk-do (KR)

(73) Assignee: WONKWANG UNIVERSITY CENTER FOR INDUSTRY-ACADEMY COOPERATION, Jeollabuk-Do (KR)

( * ) Notice: Subject to any disclaimer, the term of this patent is extended or adjusted under 35 U.S.C. 154(b) by 81 days.

(21) Appl. No.: 15/550,606

(22) PCT Filed: May 27, 2016

(86) PCT No.: PCT/KR2016/005628
§ 371 (c)(1),
(2) Date: Aug. 11, 2017

(87) PCT Pub. No.: WO2017/171134
PCT Pub. Date: Oct. 5, 2017

(65) Prior Publication Data
US 2018/0071180 A1    Mar. 15, 2018

(30) Foreign Application Priority Data

Mar. 28, 2016 (KR) .................. 10-2016-0036702

(51) Int. Cl.
*A61K 8/21*  (2006.01)
*A61Q 11/00*  (2006.01)
*A61K 33/16*  (2006.01)
*A61K 8/9767*  (2017.01)
*A61K 8/34*  (2006.01)
*A61K 8/46*  (2006.01)
*A61K 45/06*  (2006.01)
*A61K 31/015*  (2006.01)
*A61K 31/05*  (2006.01)
*A61K 31/12*  (2006.01)
*A61K 31/352*  (2006.01)

(52) U.S. Cl.
CPC .................. *A61K 8/21* (2013.01); *A61K 8/34* (2013.01); *A61K 8/46* (2013.01); *A61K 8/9767* (2017.08); *A61K 31/015* (2013.01); *A61K 31/05* (2013.01); *A61K 31/12* (2013.01); *A61K 31/352* (2013.01); *A61K 33/16* (2013.01); *A61K 45/06* (2013.01); *A61Q 11/00* (2013.01)

(58) Field of Classification Search
None
See application file for complete search history.

(56) References Cited

U.S. PATENT DOCUMENTS

2007/0105975 A1   5/2007   Orlowski et al.
2008/0119588 A1   5/2008   Orlowski et al.

FOREIGN PATENT DOCUMENTS

KR    10-2015-0123988    11/2015

OTHER PUBLICATIONS

Borate et al., Preliminary Phytochemical Studies and Evaluation of Antibacterial Activity of Psoralea corylifolia Seed Extract, 2014, American Journal of Phytomedicine and Clinical Therapeutics, vol. 2, Issue 1, pp. 95-101 (Year: 2014).*
Kabra, P. et al., "Medicinal Plants in the Treatment of Dental Caries", Asian Jour. Of Oral Health & Allied Sciences, 2(1):12-16 (Apr. 2012).
Gerhäuser, C., "Broad Spectrum Antiinfective Potential of Xanthohumol from Hop (*Humulus lupulus* L.) in Comparison with Activities of Other Hop Constituents and Xanthohumol Metabolites", M. Nutr. Food Res., 49:827-831, Wiley-VCH Verlag GmbH & Co. KGaA, Weinheim, Germany (2005).
Patil, V.C., "Synthesis and In Vitro Antiplaque Activity of Chalcone, Flavonol and Flavanol Derivatives", Int. Jour. Of Pharm. Sci and Res., 3(12):5006-5014, Panchkula, India (Dec. 2012).
English Translation of International Search Report for PCT/KR2016/005628, dated Dec. 27, 2016.

* cited by examiner

*Primary Examiner* — Nannette Holloman
(74) *Attorney, Agent, or Firm* — Cantor Colburn LLP

(57) ABSTRACT

The present invention relates to a pharmaceutical composition for prevention and treatment of dental caries comprising a fluoride varnish and an antibacterial substance as active ingredients. The fluoride varnish composition comprising xanthorrhizol, bakuchiol, bavachalcone, isobavachromene or bavachromene according to the present invention exhibits significant antibacterial activities against the strain *Streptococcus mutans* (*S. mutans*), which causes dental caries. In particular, the composition exhibits remarkable antibacterial activities compared xanthorrhizol, bakuchiol, bavachalcone, isobavachromene, bavachromene or a fluoride varnish. Therefore, the fluoride varnish comprising xanthorrhizol, bakuchiol, bavachalcone, isobavachromene or bavachromene can be usefully used for prevention and treatment of dental caries.

11 Claims, 7 Drawing Sheets

| | 1 16mM | 2 8mM | 3 4mM | 4 2mM | 5 1mM | 6 0.5mM | 7 0.25mM | 8 0.125mM | 9 0.062mM | 10 0.031mM | 11 0.015mM | 12 0.007mM |
|---|---|---|---|---|---|---|---|---|---|---|---|---|
| A No. 1-1 | 0.3590 | 0.2250 | 0.1040 | 0.0740 | 0.0580 | 0.0530 | 0.0530 | 0.0490 | 0.0470 | 0.2530 | 0.1730 | 0.1890 |
| B No. 1-2 | 0.2550 | 0.1450 | 0.1650 | 0.1100 | 0.0700 | 0.0460 | 0.0480 | 0.0490 | 0.0490 | 0.0440 | 0.0480 | 0.1200 |
| C No. 2 Bakuchiol | 0.6680 | 0.4360 | 0.5960 | 0.3450 | 0.2010 | 0.1090 | 0.0710 | 0.0580 | 0.0480 | 0.0450 | 0.0460 | 0.1340 |
| D Bacteria | 0.0370 | 0.2410 | 0.3720 | 0.3940 | 0.3710 | 0.3540 | 0.3420 | 0.3560 | 0.3250 | 0.2130 | 0.3540 | 0.1810 |
| E No. 3 Bavachalone | 0.9040 | 0.7360 | 0.9670 | 0.5920 | 0.6220 | 1.2980 | 0.8910 | 0.8910 | 0.1640 | 0.0850 | 0.0720 | 0.1590 |
| F No. 4 Isobava | 0.6540 | 0.9320 | 0.2900 | 0.4830 | 0.3900 | 0.3160 | 0.1770 | 0.1080 | 0.0830 | 0.0690 | 0.0750 | 0.1750 |
| G No. 5 Bava | 1.5140 | 0.9470 | 0.4990 | 0.6590 | 0.4610 | 0.3200 | 0.1800 | 0.1070 | 0.0880 | 0.0710 | 0.2900 | 0.1940 |
| H Medium | 0.0360 blank | | | | 0.2370 Bacteria | 0.2140 | 0.1980 | 0.3800 | 0.1760 | 0.2490 | 0.1990 | 0.1660 |

COMPOSITION OF MATERIALS CONTAINING FLUORIDE VARNISH AND ANTIBACTERIAL AGENTS FOR PREVENTION AND TREATMENT OF DENTAL CARIES

TECHNICAL FIELD

The present invention relates to an antibacterial fluoride varnish which exhibits significant antibacterial activities against *Streptococcus mutans*, obtained by adding an antibacterial substance to a fluoride varnish that sustainedly releases fluoride over a prolonged period of time.

BACKGROUND ART

Teeth in the oral cavity are exposed to continuous demineralization and remineralization. When carbohydrate remains on the tooth surface, bacteria in dental plaque are activated to produce acid, resulting in a decrease in pH and thus demineralization. When calcium and phosphate ions deposit and as a result the pH increases, remineralization takes place (Margeas, 2006).

The usefulness of fluoride-releasing agents for remineralization of enamel has been demonstrated by several studies (Burke et al., 2006; Rodrigues et al., 2008). Tooth enamel is composed of minerals, which are mainly hydroxyapatite. When a high concentration of fluoride is applied, calcium fluoride is formed on the surface of teeth. However, a study has shown that calcium fluoride easily dissolves in saliva or an alkaline solution (Seppa, 2004). Also, a study has demonstrated that calcium fluoride does not provide effective anti-caries action (Delbem et al., 2009). When a low concentration of fluoride is applied, fluorapatite is formed within the crystal structure of enamel. It has been reported that fluorapatite is more resistant to demineralization than hydroxyapatite and facilitates remineralization, thus being effective in preventing dental caries (Seppa, 2004).

There are many ways to prevent dental caries, such as oral hygiene, pit and fissure sealant, dietary control, application of fluoride, etc. Fluoride is administered systemically or topically. Examples of the method of systemic administration includes a systemic intake of fluorinated tap water or an intake of fluoride tablets. Examples of the method of topical application include a fluoride varnish, a fluoride gel, an aqueous sodium fluoride solution, a fluoride foam, a fluoride toothpaste, etc. Fluoride varnish is viscous and thus readily adheres to teeth. It hardens when contacted with saliva (Delbem et al., 2009). As a result, fluoride is released to the enamel surface, dental plaque, and saliva. Fluoride varnish is widely used because it releases fluoride over a prolonged period of time compared to other fluoride agents (Modeer et al., 1984; Petersson, 1993; Delbem et al., 2009).

Several studies have compared fluoride varnish with other topical fluoride agents. Tewari et al. (1990) compared Duraphat, 2% sodium fluoride aqueous solution and 1.23% APF gel. The study reported that 2 years and 6 months after the application of fluoride, dental caries decreased by 28% in the 2% sodium fluoride aqueous solution and by 37% in the APF while dental caries decreased at a high rate of 74% in the fluoride varnish.

Clinical studies in Europe have demonstrated that fluoride varnish reduced dental caries by 18%-77% (de Bruyn and Arends, 1987).

Fluoride varnish is composed of a resin base, a solvent, and fluoride. Examples of the resin base include colophony, polyurethane, resin modified glass ionomer, methyl salicylate, polyamide, etc. Most fluoride varnishes use ethanol as the solvent, but some products use ethyl acetate. Most fluoride varnishes use 5% NaF as the fluoride, but some products use difluorosilane. A study by Attin et al. (2005) compared a fluoride varnish (Mirafluorid) made of water-soluble resin with a fluoride varnish (Duraphat) of natural resin. The study showed that the fluoride varnish of natural resin exhibits a higher level of fluoride deposition on the tooth surface than the fluoride varnish of water-soluble resin. It has been reported that although fluoride varnish has a fluoride concentration almost twice that of APF gel, it is not harmful to children (Seppa, 2004). A study by Roberts and Longhurst (1987) reported that the general dose of fluoride varnish for children aged 2 to 14 years is 5.2 mg, and that this amount of fluoride does not cause acute toxicity. Because fluoride varnish adheres to the tooth surface, fluoride can be gradually absorbed. However, a part of the fluoride is discharged immediately without being absorbed into the body. Even in Europe, where fluoride varnish has been used for a long time, there have been no report of fluoride-induced acute poisoning (Shen and Autio-Gold, 2002). According to the WHO, when 1 mg or more of fluoride per kg of body weight is ingested, acute fluoride poisoning will develop. However, when 5.2 mg of 5% fluoride varnish is applied to the oral cavity as in the above study, 0.26 mg of fluoride will be ingested. Thus, fluoride varnish is safer for our body than any other fluoride agent.

The effective concentration to prevent dental caries varies depending on studies. Featherstone (1999) reported that when the fluoride concentration in saliva is 0.03 ppm, dental caries can be prevented. Leverett et al. (1993) and Featherstone (1999) reported that when the fluoride concentration in saliva is 0.04 ppm or higher, the risk of dental caries decreases. Gibbs et al. (1995) reported that a fluoride concentration of 0.06 ppm leads to recalcification of enamel. Page (1991) demonstrated that brushing with a toothpaste containing fluoride results in the fluoride concentration in saliva of 0.014 ppm, which prevents demineralization for 72 hours in a weakly acidic solution and produces anticaries effects.

Fluoride varnish rapidly releases fluoride at early stage, and then the release amount of fluoride sharply decreases. In the study of Shen and Autio-Gold (2002), a fluoride varnish released 97% of the fluoride ions for 9 days. Therefore, it is necessary to produce a fluoride varnish which can maintain an effective concentration to prevent dental caries for a prolonged period of time.

*Streptococcus mutans* is a major pathogen that affects dental caries (Bowden and Li, 1997)). The bacterium strongly adheres to the tooth surface and produces an acid that lowers pH from fermentable carbohydrates, which leads to mineral loss. It is believed that dental plaque is a cause of dental caries because it allows the strong adhesion of *S. mutans* (Bowden and Li (1997), Pinar Erdem et al. (2012)). Studies have shown that the number of *S. mutans* decreased after application of fluoride varnish (Jeevarathan et al., 2007). However, Beltran-Aguilar et al. (2000) reported that when Duraphat fluoride varnish was used in children, it did not significantly affect the number of *S. mutans* in saliva and in the portions to which dental plaque is attached. The researchers assumed that this was because the effect of inhibition of dental caries by fluoride varnish results from remineralization of early caries lesions. Therefore, it is necessary to confirm whether fluoride varnish itself has antibacterial effect against *S. mutans*. In addition, it is necessary to evaluate which antibacterial substance mixed with a fluoride varnish of which material exhibits the maximum antibacterial effect.

To date, few studies have evaluated the antibacterial properties of a fluoride varnish mixed with an antibacterial substance, except that mixed with chlorhexidine. Chlorhexidine has been reported to exhibit antibacterial, anticaries, and remineralization effects and have some toxicity (Pinar Erdem et al., 2012). Chlorhexidine is known to be particularly effective against *S. mutans*. It is also clinically used as a mouthwash or a root canal treatment (Keltjens et al., 1992). According to a study by Kitagawa et al. (2014), 12-methacryloyloxydodecylpyridinium bromide (MDPB), a quaternary ammonium compound-based antibacterial primer, exhibits antibacterial effects only on the site directly contacted with this material. When dental plaque covers the teeth after this material is applied, it cannot affect the bacteria in the oral cavity. Recently, much attention has been paid to studies on natural substances, in order to increase antibacterial effects and reduce side effects of antibacterial substance (Cunha, 2001). Among them, one study reported that propolis has low toxicity and that propolis extract exhibits antibacterial effects on dental caries bacteria. Also, studies have been reported on the addition of propolis to varnish (De Luca et al., 2014). Xanthorrhizol has been reported to exhibit excellent antibacterial activities against oral bacteria, particularly against *S. mutans* (Shim et al., 2000). It is also necessary to produce a fluoride varnish which is free from cytotoxicity. Further, it is necessary to observe the change in the hardness of the tooth surface and in the surface composition of the tooth due to the release of fluoride.

Therefore, the present inventors have made efforts to develop a composition having significant antibacterial activities against *S. mutans* by adding an antibacterial substance to a fluoride varnish. As a result, the present inventors have found that when xanthorrhizol, bakuchiol, bavachalcone, isobavachromene or bavachromene is added to a fluoride varnish, the fluoride varnish exhibits remarkable antibacterial activities as compared with a group treated with a fluoride varnish alone and groups treated with each of the antibacterial substances. Consequently, the present inventors have found that a fluoride varnish to which an antibacterial substance has been added can be usefully used for prevention and treatment of dental caries, and thus completed the present invention.

SUMMARY OF INVENTION

Technical Problem

The objective of the present invention is to provide an antibacterial fluoride varnish with significant antibacterial activities against *Streptococcus mutans*, obtained by adding an antibacterial substance to a fluoride varnish that sustainedly releases fluoride over a prolonged period of time.

Solution to Problem

In order to achieve the above objective, the present invention provides a pharmaceutical composition for prevention and treatment of dental caries comprising a fluoride varnish and an antibacterial substance as active ingredients.

In addition, the present invention provides a pharmaceutical composition for prevention and treatment of dental caries comprising a chalcone-based compound or a pharmaceutically acceptable salt thereof as an active ingredient.

Advantageous Effects of Invention

The fluoride varnish composition comprising xanthorrhizol, bakuchiol, bavachalcone, isobavachromene or bavachromene according to the present invention exhibits significant antibacterial activities against the strain *Streptococcus mutans* (*S. mutans*). In particular, the composition of the present invention exhibits significant antibacterial activities compared with the groups treated with xanthorrhizol, bakuchiol, bavachalcone, isobavachromene, bavachromene, or a fluoride varnish alone. Therefore, the fluoride varnish comprising xanthorrhizol, bakuchiol, bavachalcone, isobavachromene or bavachromene according to the present invention can be usefully used for prevention and treatment of dental caries.

BRIEF DESCRIPTION OF DRAWINGS

Positive control group: a group treated with 10 μL/mL of ampicillin alone; and

Negative control group: a group treated with PBS alone.

Positive control group: a group treated with 10 μL/mL of ampicillin alone; and

Negative control group: a group treated with PBS alone.

1: a group treated with bavachalcone alone.

2: a group treated with PBS, which is a negative control group; and

3: a group treated with a fluoride varnish mixed with bavachalcone of the present invention.

Positive control group: a group treated with 10 μL/mL of ampicillin alone; and

Negative control group: a group treated with PBS alone.

DESCRIPTION OF EMBODIMENTS

[Embodiments]

Hereinafter, the present invention will be described in detail.

The present invention provides a pharmaceutical composition for prevention and treatment of dental caries comprising a fluoride varnish and an antibacterial substance as active ingredients.

Preferably, the composition exhibits the effect of prevention and treatment of dental caries through antibacterial activities against *Streptococcus mutans*.

Preferably, the fluoride varnish is prepared by the following method, but is not limited thereto:

1) mixing a hydrogenated rosin; a solvent; and a fluoride compound; and 2) stirring the resultant mixture in a water bath at 70 to 95° C. for 25 to 40 minutes.

The ratio of the hydrogenated rosin; the solvent; and the fluoride compound of step 1) above may be 30 to 65 wt %: 35 to 65 wt %: 1 to 10 wt %, more specifically 35 to 55 wt %: 40 to 60 wt %: 2 to 8 wt %, even more specifically 45 wt %: 50 wt %: 5 wt %, based on the total weight of the mixture.

The solvent of step 1) may be one or more selected from the group consisting of distilled water, dimethyl sulfoxide (DMSO), isoamyl propionate, hydrogen fluoride (HF), ethanol, and ethyl acetate. More specifically, it may be ethanol or ethyl acetate.

The fluoride compound of step 1) may be one or more selected from the group consisting of HF, $NH_4F$, NaF, KF, $Na_2FPO_4$, $K_2FPO_4$, $CaF_2$, $TiF_4$, $Ca_5(PO_4)_3F$, $H_2F_2Si$ (difluorosilane), $C_{16}H_{36}FN$ and $SnF_2$. More specifically, it may be NaF. The fluoride compounds may be used alone or as a mixture of two or more thereof.

The hydrogenated rosin refers to a rosin with hydrogen added, combined with hydrogen, or cured with hydrogen.

Preferably, the antibacterial substance is one or more selected from the group consisting of bakuchiol represented by Chemical Formula 1 below, bavachalcone represented by Chemical Formula 2 below, isobavachromene represented by Chemical Formula 3 below, bavachromene represented by Chemical Formula 4 below and xanthorrhizol represented by Chemical Formula 5 below.

[Chemical Formula 1]

[Chemical Formula 2]

[Chemical Formula 3]

[Chemical Formula 4]

[Chemical Formula 5]

In a specific example of the present invention, the present inventors screened antibacterial substances having antibacterial activities against *Streptococcus mutans* (*S. mutans*). As a result, it was confirmed that among a total of 100 substances, xanthorrhizol, bavachalcone, bakuchiol, isobavachromene and bavachromene exhibit antibacterial activities against *S. mutans* (see FIG. 1).

The present inventors also investigated the antibacterial effect of fluoride varnishes of hydrogenated rosin mixed with an antibacterial substance. As a result, it was confirmed that fluoride varnishes mixed with an antibacterial substance have enhanced effects compared with a fluoride varnish itself. Especially, a fluoride varnish mixed with bavachalcone was found to exhibit significant antibacterial activities (see FIG. 2, FIG. 3, Table 2 and Table 3).

Also, the present inventors investigated the antibacterial activities of fluoride varnishes mixed with an antibacterial substance as compared with groups treated with an antibacterial substance alone. As a result, it was confirmed that the fluoride varnishes mixed with an antibacterial substance of the present invention show similar results to the groups treated with an antibacterial substance alone in the formation of an inhibition zone, but bring about a remarkable difference in the formation of a Semi-inhibition zone. Also, it was confirmed that the fluoride varnishes comprising an antibacterial substance of the present invention exhibit significant antibacterial activities in a larger region than the groups treated with an antibacterial substance alone, although bacteria cannot be completely eradicated in a Semi-inhibition zone (See FIGS. 4 to 6 and Table 4).

In addition, the present inventors investigated the minimum inhibitory concentration and the minimal bactericidal concentration of antibacterial substances using *S. mutans*, which is related to dental caries, as the strain. As a result, it was confirmed that when xanthorrhizol (BioAlpha), bakuchiol, bavachalcone and isobavachromene has the lowest MIC, and that bakuchiol has the lowest MBC, followed by bavachalcone and xanthorrhizol (BioAlpha) (see Table 5 and FIG. 7).

Thus, the fluoride varnish composition comprising xanthorrhizol, bakuchiol, bavachalcone, isobavachromene or bavachromene according to the present invention exhibits significant antibacterial activities against the strain *Streptococcus mutans*, which causes dental caries. Particularly, the composition of the present invention exhibits significant antibacterial activities in a larger region compared with the groups treated with xanthorrhizol, bakuchiol, bavachalcone, isobavachromene, bavachromene or a fluoride varnish alone. Therefore, the fluoride varnish comprising xanthorrhizol, bakuchiol, bavachalcone, isobavachromene or bavachromene can be usefully used for prevention and treatment of dental caries.

The composition of the present invention may further contain a polymerization inhibitor, a pigment, a coloring agent, a fluorescent agent, an ultraviolet absorber, a sweetener, a flavor, wax, xylitol for neutralization of pH, carbonate apatite and calcium phosphate for remineralization of teeth, sodium phosphate, calcium sulfate dihydrate, wax, hexane, polyisocyanate having the properties of adhering to teeth, glutaraldehyde, MDP (10-methacryloyloxydecyl dihydrogen phosphate), etc. in an amount that does not impair the effect of the present invention. Also, preferably the composition of the present invention is applied parenterally (e.g., by application). It is preferable to apply 4 mg to 6 mg of 5% fluoride varnish per tooth, or 0.25 mL thereof per deciduous tooth and 0.4 mL thereof per permanent teeth. It is preferable to apply it to the whole teeth.

In addition, the composition comprising a fluoride varnish and an antibacterial substance according to the present invention can be formulated into a mouth rinse, a teeth desensitizer, an antibacterial dental adhesive, a dental filling materials, a dental restorative material, a dental root canal filling materials, a dental root canal sealer, a pit and fissure sealant, a dental coating material, or a dental cement according to known methods.

The present invention also provides a method for treatment or prevention of dental caries comprising the step of administering or applying a composition comprising a pharmaceutically effective amount of a fluoride varnish and an antibacterial substance as active ingredients to a subject afflicted with dental caries.

In addition, the present invention provides the use of a composition comprising a fluoride varnish and an antibacterial substance as active ingredients for the preparation of pharmaceutical compositions for prevention and treatment of dental caries.

Specifically, the fluoride varnish composition comprising xanthorrhizol, bakuchiol, bavachalcone, isobavachromene or bavachromene according to the present invention exhibits significant antibacterial activities against the strain *Streptococcus mutans* (*S. mutans*), which causes dental caries. In particular, the composition of the present invention exhibits significant antibacterial activities in a larger region than the groups treated with xanthorrhizol, bakuchiol, bavachalcone, isobavachromene, bavachromene or a fluoride varnish alone. Therefore, the fluoride varnish comprising xanthorrhizol, bakuchiol, bavachalcone, isobavachromene or bavachromene according to the present invention can be usefully used for prevention and treatment of dental caries.

The present invention also provides a pharmaceutical composition for prevention and treatment of dental caries comprising a chalcone-based compound or a pharmaceutically acceptable salt thereof as an active ingredient.

Preferably, the chalcone-based compound is bavachalcone represented by Chemical Formula 2 below, isobavachromene represented by Chemical Formula 3 below or bavachromene represented by Chemical Formula 4 below, but is not limited thereto:

[Chemical Formula 2]

[Chemical Formula 3]

[Chemical Formula 4]

In addition, the composition comprising an antibacterial substance according to the present invention can be formulated into a mouth rinse, a teeth desensitizer, an antibacterial dental adhesive, a dental filling materials, a dental restorative material, a dental root canal filling materials, a dental root canal sealer, a pit and fissure sealant, a dental coating material, or a dental cement according to known methods.

In a specific example of the present invention, the present inventors screened antibacterial substances having antibacterial activities against *Streptococcus mutans* (*S. mutans*). As a result, it was confirmed that among a total of 100 substances, bavachalcone, isobavachromene and bavachromene exhibit antibacterial activities against *S. mutans* (see FIG. 1).

Thus, the chalcone-based compound of the present invention exhibits antibacterial activities against *S. mutans*, and thus can be usefully used as a pharmaceutical composition for prevention and treatment of dental caries.

The present invention encompasses not only chalcone-based compounds but also pharmaceutically acceptable salts thereof, all solvates, hydrates or racemates that can be prepared therefrom, and stereoisomers thereof.

The chalcone-based compound of the present invention can be used in the form of a pharmaceutically acceptable salt. Useful salts are acid addition salts formed from a pharmaceutically acceptable free acid. The acid addition salts are obtained from inorganic acids such as hydrochloric acid, nitric acid, phosphoric acid, sulfuric acid, hydrobromic acid, hydriodic acid, nitrous acid or phosphorous acid and nontoxic organic acids such as aliphatic mono- and di-carboxylate, phenyl-substituted alkanoate, hydroxy alkanoate, alkanedioate, aromatic acids, aliphatic and aromatic sulphonic acids. Examples of the pharmaceutically nontoxic salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, hydroxybutyrate, glycolate, malate, tartrate, methanesulfonate, propanesulfonate, naphthalene-1-sulfonate, naphthalene-2-sulfonate and mandelate.

The acid addition salt according to the present invention can be prepared by a conventional method, for example, by dissolving a chalcone-based compound in an excess aqueous acid solution and then precipitating the resultant salt in a water-miscible organic solvent such as methanol, ethanol, acetone or acetonitrile. Also, it can be prepared by drying the mixture by evaporating the solvent or an excess acid therefrom or by suction filtration of the precipitated salt.

In addition, pharmaceutically acceptable metal salts can be prepared by using a base. Alkali metal or alkaline earth metal salts are obtained, for example, by dissolving a compound in an excess alkali metal hydroxide or alkaline earth metal hydroxide solution, filtering the undissolved compound salt, and evaporating and drying the filtrate. Metal salts suitable for pharmaceutical use are sodium, potassium or calcium salts. Also, silver salts corresponding thereto are obtained by reacting an alkali metal or alkaline earth metal salt with a suitable silver salt (for example, silver nitrate).

When the composition is formulated, generally used diluents or excipients such as fillers, extenders, binders, wetting agents, disintegrants, surfactants, etc. are used.

Solid preparations for oral administration include tablets, pills, powders, granules, capsules, troches, etc. These solid preparations are prepared by mixing at least one chalcone-based compound of the present invention with at least one excipient, for example, starch, calcium carbonate, sucrose or lactose, or gelatin, etc. Further, lubricants such as magnesium stearate, talc, etc. are used in addition to simple excipients. Liquid preparations for oral administration include suspensions, solutions, emulsions, syrups, etc. They may comprise various excipients such as a wetting agent, a sweetener, a flavoring agent, a preservative, TEOS, etc., as well as water, liquid paraffin, and wax, which are generally used simple diluents.

Preparations for parenteral administration include sterile aqueous solutions, non-aqueous solutions, suspensions, emulsions, freeze-dried formulations, suppositories, etc. Propylene glycol, polyethylene glycol, vegetable oil such as olive oil, injectable esters such as ethyl oleate, etc. may be used for the non-aqueous solutions or suspensions. Witepsol, macrogol, tween, cacao butter, laurinum, glycerol, gelatin, etc. may be used as matrices for the suppositories.

The composition according to the invention is administered in a pharmaceutically effective amount. As used herein, "pharmaceutically effective amount" refers to an amount sufficient to treat a disease at a reasonable benefit/risk rate applicable to medical treatment. The effective dose can be determined based on factors including the type and severity of the patient's disease, activity of the drug, sensitivity to the drug, administration time, administration route, excretion rate, duration of treatment and co-administered drugs, and other factors well known in the medical field. The composition of the present invention may be administered alone or in combination with another therapeutic agent. It may be administered sequentially or simultaneously with a conventional therapeutic agent, and may be administered in a single dose or multiple doses. It is important to administer a minimum amount that can yield the maximum effect without side effects by taking into account all of the factors. Such amount can be easily determined by those skilled in the art.

Specifically, the effective dose of the compound according to the present invention may vary depending on the age, gender and body weight of the patient. In general, 0.1 mg to 100 mg, preferably 0.5 mg to 10 mg per kg of the body weight may be administered every day, every other day, or 1 to three times a day. However, the dose may be varied depending on administration route, severity of the disease, gender, body weight, age, etc. Therefore, the dose does not in any way limit the scope of the present invention.

The present invention also provides a method for treatment or prevention of dental caries comprising the step of administering a pharmaceutically effective amount of a chalcone-based compound or a pharmaceutically acceptable salt thereof to a subject afflicted with dental caries.

In addition, the present invention provides the use of a chalcone-based compound for the preparation of compositions for prevention and treatment of dental caries.

Specifically, the chalcone-based compound of the present invention exhibits antibacterial activities against *S. mutans*, and thus can be usefully used for prevention or treatment of dental caries.

In addition, the present invention provides a health food for prevention and improvement of dental caries comprising a chalcone-based compound or a pharmaceutically acceptable salt thereof as an active ingredient.

Preferably, the chalcone-based compound is bavachalcone represented by Chemical Formula 2 above, isobavachromene represented by Chemical Formula 3 above, or bavachromene represented by Chemical Formula 4 above, but is not limited thereto.

In a specific example of the present invention, the present inventors screened antibacterial substances having antibacterial activities against *Streptococcus mutans* (*S. mutans*). As a result, it was confirmed that among a total of 100 substances, bavachalcone, isobavachromene and bavachromene exhibit antibacterial activities against *S. mutans* (see FIG. 1).

Therefore, the chalcone-based compound of the present invention exhibits antibacterial activities against *S. mutans*, and thus can be usefully used as a health food for prevention and improvement of dental caries.

When the compound of the present invention is used as a food or beverage additive, the compound may be added directly or used in combination with another food or food ingredient, and may be appropriately used according to a conventional method. The mixing amount of the compound may be appropriately determined according to the intended use (for prevention, health or therapeutic treatment). When ingested for a long time for the purpose of health and hygiene or health control, the compound causes no problem in safety. Thus, the compound can be taken for a long period of time. The type of the food is not particularly limited. Examples of the food to which the substance may be added include meats, sausages, breads, chocolates, candies, gellies, snacks, confectioneries, pizzas, ramen, noodles, gums, dairy products including ice creams, milk, yogurts, cheeses, various types of soups, beverages, teas, drinks, alcoholic beverages, vitamin complexes, etc. When it is formulated into a beverage, the beverage may further include a liquid ingredient, for example but not limited to, various flavoring agents or natural carbohydrates, etc. as an additional ingredient in addition to the compound of the present invention, as do common beverages. Examples of the natural carbohydrates include monosaccharides (e.g., glucose, fructose, etc.), disaccharides (e.g., maltose, sucrose, etc.) and polysaccharides (e.g., conventional sugars such as dextrin, cyclodextrin, etc.) and sugar alcohols such as xylitol, sorbitol, erythritol, etc. In general, the natural carbohydrate is included in an amount of about 1 to 20 g, preferably about 5 to 12 g per 100 mL of the composition of the present invention. Examples of the flavoring agents include natural flavoring agents (e.g., thaumatin and *stevia* extracts (e.g., rebaudioside A, glycyrrhizin, etc.) and synthetic flavoring agents (e.g., saccharin, aspartame, etc.).

In another embodiment, the food composition of the present invention may contain various nutrients, a vitamin, a mineral (electrolyte), a flavoring agent such as a synthetic flavoring agent and a natural flavoring agent, a coloring agent and an improving agent (cheese, chocolate, etc.), pectic acid or a salt thereof, an organic acid, a protective colloidal thickening agent, a pH controlling agent, a stabilizing agent, a preservative, glycerin, alcohol, a carbonating agent as used in carbonated beverages, etc. Additionally, the food composition of the present invention may contain fruit flesh for the preparation of fruit juice beverages and vegetable juices. These ingredients may be used alone or as a mixture thereof. In general, these additives are used in an amount of 0.001 to 50 parts by weight based on the total weight of the composition.

In addition, the present invention provides the use of a chalcone-based compound for the preparation of health foods for prevention and improvement of dental caries.

Specifically, the chalcone-based compound of the present invention exhibits antibacterial activities against *S. mutans*, and thus can be usefully used as a health food for prevention and improvement of dental caries.

Hereinafter, the present invention will be described in further detail with reference to examples and test examples. It is to be understood, however, that these examples are for illustrative purposes only and are not intended to limit the scope of the present invention.

EXAMPLES

Example 1: Preparation of Fluoride Varnish of Hydrogenated Rosin 45 wt % (9 g) of hydrogenated rosin (KR-610, ARAKAWA) was used to prepare a fluoride varnish of hydrogenated rosin. 50 wt % (10 g) of ethanol (absolute ≥99.7%, Merck KGaA) was used as the solvent and 5 wt % (1 g) of NaF was used. The ingredients were mixed for 30 minutes at 240 rpm with an overhead stirrer on a hot plate (RCH-3, Tokyo Rikakikai Co., Ltd., Tokyo, Japan) for heating in a water bath at 90° C. to prepare a fluoride varnish of hydrogenated rosin.

Example 2: Preparation of Fluoride Varnish of Hydrogenated Rosin Mixed with Antibacterial Substance Antibacterial substance powders were dissolved in DMSO to 100 mM and stored. It was diluted with DMSO to prepare 20 mM and 2 mM antibacterial substances. Then, each of them were mixed with a fluoride varnish prepared in Example 1 at a ratio of 1:1 to prepare fluoride varnishes mixed with 10 mM or 1 mM antibacterial substance Specifically, 10 μL of 20 mM antibacterial substance and 10 μL of fluoride varnish were mixed (mixing 20 mM antibacterial substance and fluoride varnish at a ratio of 1:1) to prepare a fluoride varnish mixed with 10 mM antibacterial substance. In addition, 10 μL of 2 mM antibacterial substance and 10 μL of fluoride varnish were mixed (mixing 2 mM antibacterial substance and fluoride varnish at a ratio of 1:1) to prepare a fluoride varnish mixed with 1 mM antibacterial substance.

Test Example 1: Screening for Antibacterial Substances Having Antibacterial Activities Against *Streptococcus mutans* (*S. mutans*)

In order to develop an antibacterial fluoride varnish that can most effectively inhibit *S. mutans* when added to a fluoride varnish, the antibacterial properties of the following six antibacterial substances were evaluated using *S. mutans* (ATCC 25175), which is related to dental caries, as a strain, according to the agar diffusion test:

|  | Chemical structure | Code | Company | Concentration |
|---|---|---|---|---|
| Xanthorrhiol | | 1-1 | Santa Cruz | 0.1 mM, 1 mM, 10 mM |
| | | 1-2 | BioAlpha | 0.1 mM, 1 mM, 10 mM |
| Bakuchiol | | 2 | Santa Cruz | 0.1 mM, 1 mM, 10 mM |
| Bavachalcone | | 3 | Chemfaces | 0.1 mM, 1 mM, 10 mM |

| Chemical structure | | Code | Company | Concentration |
|---|---|---|---|---|
| Isobavachromene | [structure] | 4 | Chemfaces | 0.1 mM, 1 mM, 10 mM |
| Bavachromene | [structure] | 5 | Chemfaces | 0.1 mM, 1 mM, 10 mM |

Specifically, *S. mutans* was primarily cultured in a BHI medium in a $CO_2$ incubator at 37°C. for 24 hours. Then, 200 µL of a suspension of *S. mutans* was inoculated into BHI and secondarily cultured for 6 hours. Then, the OD value was measured with Eppendorf Biophotometer plus. After the measurement, the bacteria were mixed with top agar and then inoculated into the agar medium containing base agar. After top agar hardened, a 6 mm diameter paper disc was placed on the agar medium.

5 µL of each of 0.1 mM, 1 mM and 10 mM antibacterial substances was dropped on the paper disc. 10 µL/ml of ampicilin was used as the positive control, and PBS was used as the negative control. After culturing in a $CO_2$ incubator at 37°C for 24 hours, the diameter of the *S. mutans* inhibition zone formed around the paper disc was measured in two perpendicular locations and the average was calculated to evaluate the antibacterial activities. The average was expressed in mm.

Figure 1:
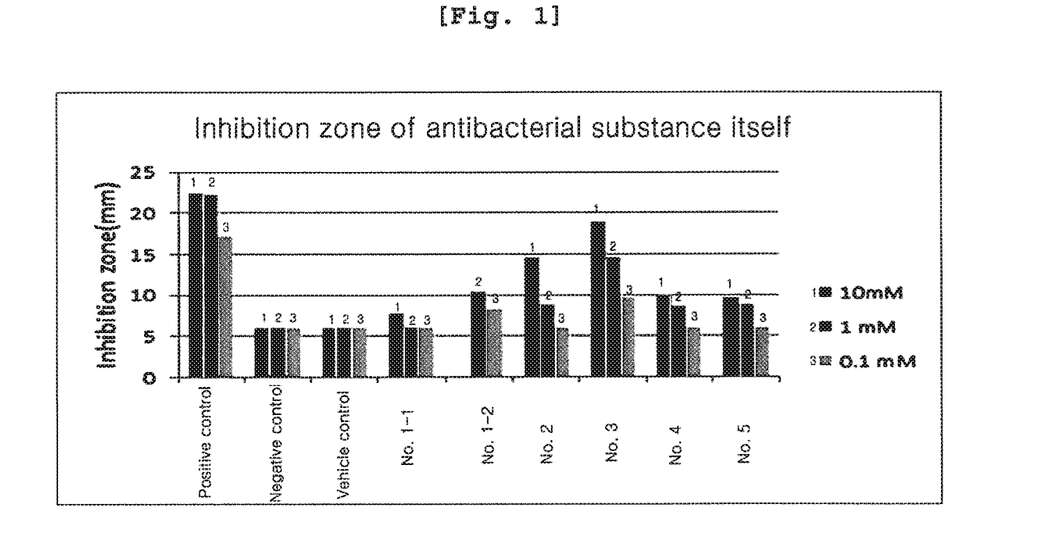
FIG. 1 is a graph showing the antibacterial activities against *Streptococcus mutans* (*S. mutans*).

As a result, as shown in FIG. 1 and Table 1, DMSO itself formed no inhibition zone around the paper disc as did the negative control. Thus, it has no antibacterial effect against *S. mutans*. When 10 mM antibacterial substance was used, bavachalcone exhibited the highest activities against *S. mutans*, followed by bakuchiol, isobavachromene, bavachromene and xanthorrhizol. When 1 mM antibacterial substance was used, bavachalcone exhibited the highest activities against *S. mutans*, followed by xanthorrhizol, bakuchiol, isobavachromene and bavachromene. When 0.1 mM antibacterial substance was used, bavachalcone and xanthorrhizol exhibited significant activities against *S. mutans* despite the low concentration (FIG. 1).

That is, as a result of screening for substances with significant antibacterial activities from a total 100 substances, it was confirmed that xanthorrhizol, bavachalcone, bakuchiol, isobavachromene and bavachromene exhibit significant antibacterial activities against *S. mutans*. Especially, bavachromene was found to exhibit significant antibacterial activities in all conditions including 10 mM, 1 mM and 0.1 mM.

TABLE 1

| | 10 mM antibacterial substance alone | 1 mM antibacterial substance alone | 0.1 mM antibacterial substance alone |
|---|---|---|---|
| Positive control group | 22.4 | 22.2 | 17.24 |
| Negative control group | 6 | 6 | 6 |

TABLE 1-continued

| | 10 mM antibacterial substance alone | 1 mM antibacterial substance alone | 0.1 mM antibacterial substance alone |
|---|---|---|---|
| Vehicle control | 6 | 6 | 6 |
| No. 1-1 | 7.75 | 6 | 6 |
| No. 1-2 | | 10.3 | 8.26 |
| No. 2 | 14.5 | 8.9 | 6 |
| No. 3 | 18.87 | 14.51 | 9.63 |
| No. 4 | 9.91 | 8.71 | 6 |
| No. 5 | 9.74 | 8.75 | 6 |

Test Example 2: Identification of Antibacterial Effects of Fluoride Varnish of Hydrogenated Rosin Mixed with Antibacterial Substance Fluoride varnishes mixed with an antibacterial substance which comprise an antibacterial substance tested in Test Example 1 were prepared according to the method described in Example 2 and the antibacterial activities thereof were tested. For the sake of accuracy, the measurement of the antibacterial activities of a fluoride varnish mixed with an antibacterial substance was repeated twice and the results were compared with each other.

Figure 2:
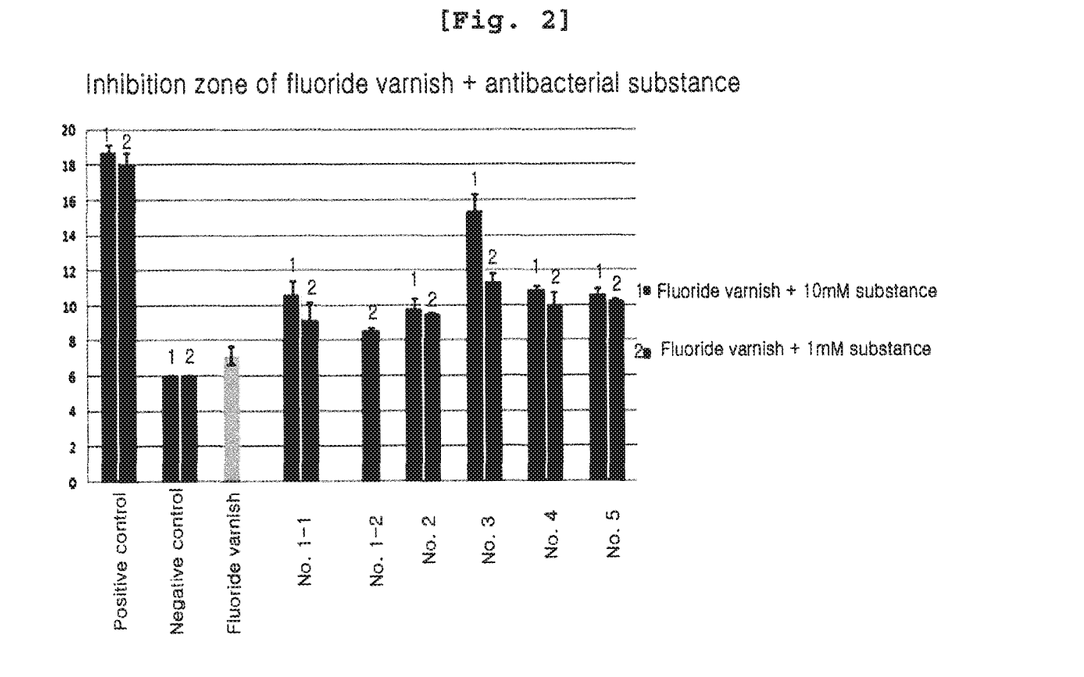
FIG. 2 is a graph showing the primary antibacterial activities of fluoride varnishes of hydrogenated rosin mixed with an antibacterial substance. The terms used are defined as follows.

As a result, as shown in FIG. 2 and Table 2, when the primary antibacterial activities of fluoride varnishes mixed with an antibacterial substance were tested, the fluoride varnish alone exhibited slight antibacterial activities against *S. mutans*, but without significance. In the case of fluoride varnishes mixed with a 1 mM or 10 mM antibacterial substance, all of those mixed with xanthorrhizol, bavachalcone, bakuchiol, isobavachromene or bavachromene exhibited significant antibacterial activities compared with a fluoride varnish alone. In particular, the antibacterial activities of a fluoride varnish mixed with bavachalcone increased by about 70% or more (FIG. 2 and Table 2).

Figure 3:
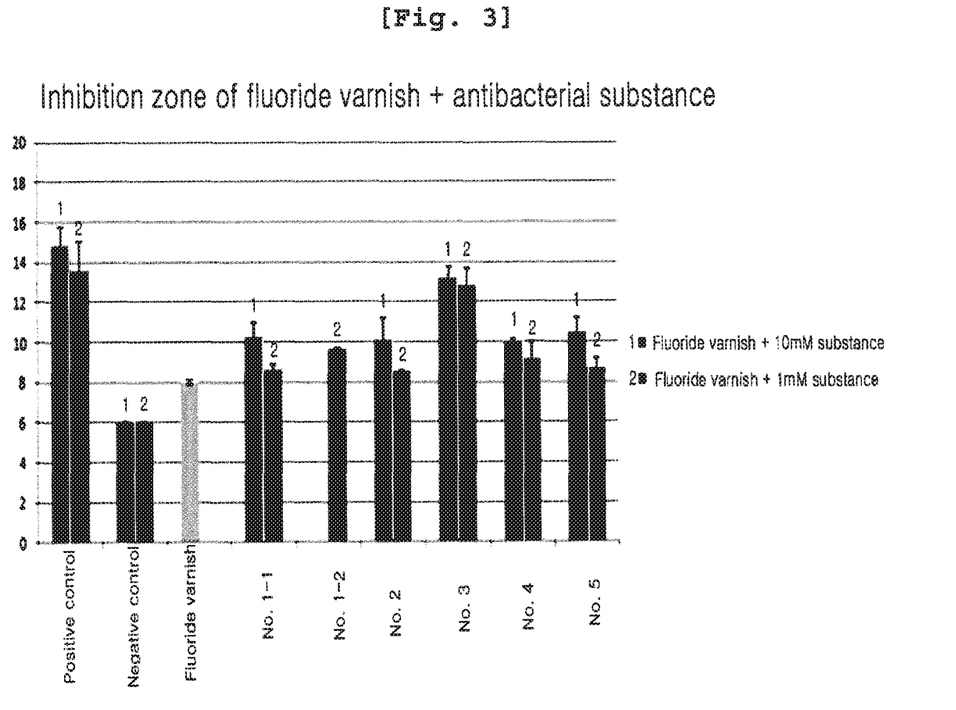
FIG. 3 is a graph showing the secondary antibacterial activities of fluoride varnishes of hydrogenated rosin mixed with an antibacterial substance. The terms used are defined as follows.

Also, as shown in FIG. 3 and Table 3, when the secondary antibacterial activities of fluoride varnishes mixed with an antibacterial substance were tested, the fluoride varnish mixed with bavachalcone exhibited remarkable antibacterial activities, as in the test for the primary activities (FIG. 3 and Table 3).

In conclusion, it was confirmed that a fluoride varnish mixed with an antibacterial substance has increased antibacterial effects compared with the fluoride varnish itself. In particular, the fluoride varnish mixed with bavachalcone was found to exhibit significant antibacterial activities.

TABLE 2

| Inhibition zone (mm) | Fluoride varnish + 10 mM substance | Fluoride varnish + 1 mM substance | Standard deviation value of fluoride varnish + 10 mM substance | deviation value of fluoride varnish + 1 mM substance |
| --- | --- | --- | --- | --- |
| Positive control group | 18.34 | | 0.371966 | |
| Negative control group | 6.00 | | 0 | |
| Fluoride varnish | 7.16 | | 0.26 | |
| Positive control group | 18.72 | 18.04875 | 0.38 | 0.64263 |
| Negative control group | 6.00 | 6.00 | 0 | 0 |
| No. 1-1 | 10.62 | 9.14 | 0.763675 | 0.97 |
| No. 1-2 | | 8.58 | 0 | 0.11 |
| No. 2 | 9.82 | 9.55 | 0.537401 | 0.04 |
| No. 3 | 15.35 | 11.31 | 0.972272 | 0.51 |
| No. 4 | 10.93 | 9.94 | 0.141421 | 0.75 |
| No. 5 | 10.60 | 10.27 | 0.325269 | 0.08 |

TABLE 3

| Inhibition zone (mm) | Fluoride varnish + 10 mM substance | Fluoride varnish + 1 mM substance | Standard deviation value of fluoride varnish + 10 mM substance | Standard deviation value of fluoride varnish + 1 mM substance |
| --- | --- | --- | --- | --- |
| Positive control group | 15.49 | | 0.58 | |
| Negative control group | 6.00 | | 0 | |
| Fluoride varnish | 7.99 | | 0.109602 | |
| Positive control group | 14.84 | 13.55 | 0.94 | 1.461 |
| Negative control group | 6.00 | 6.00 | 0 | 0 |
| No. 1-1 | 10.28 | 8.64 | 0.714178 | 0.258094 |
| No. 1-2 | | 9.65 | 0 | 0.074246 |
| No. 2 | 10.10 | 8.53 | 1.074802 | 0.074246 |
| No. 3 | 13.17 | 12.79 | 0.604576 | 0.883883 |
| No. 4 | 9.96 | 9.17 | 0.219203 | 0.823779 |
| No. 5 | 10.48 | 8.66 | 0.738927 | 0.487904 |

Test Example 3: Identification of Antibacterial Activities of Fluoride Varnish Mixed with Antibacterial Substance in Comparison with Group Treated with Antibacterial Substance Alone In order to identify the effects of the fluoride varnish mixed with an antibacterial substance of the present invention as compared with a group treated with an antibacterial substance alone, the formation of a Semi-inhibition zone was evaluated.

Specifically, the antibacterial substances themselves subjected to agar diffusion test of Test Example 1 and the Positive control group showed clearly distinguished two zones: a bacteria-containing zone and a clear zone where bacteria have been completely inhibited (inhibition zone).

Figure 4:
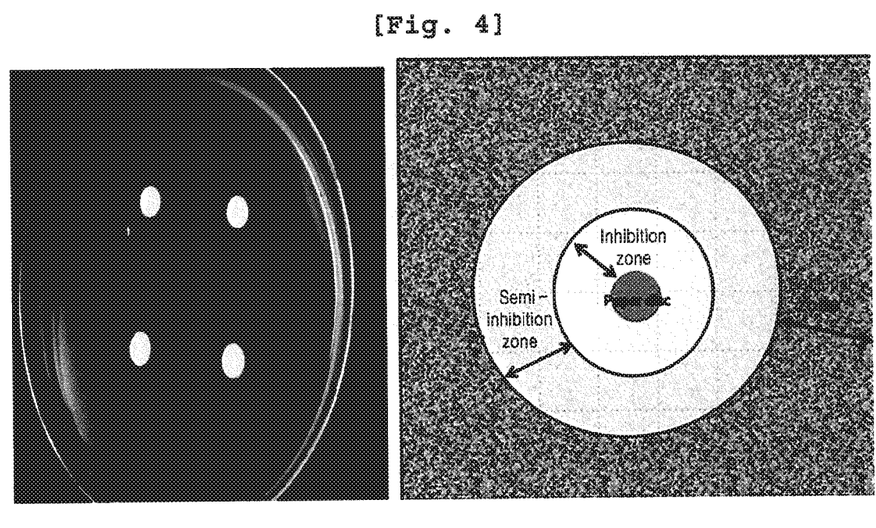
FIG. 4 shows the results of agar diffusion test. Each of the reference numerals refer to the following.

However, as shown in FIG. 4, fluoride varnishes mixed with an antibacterial substance showed three distinguished zones: a clear zone where bacteria have been completely inhibited (inhibition zone; clear zone), a zone distinct from a bacteria-containing zone with clear boundaries albeit with a lower clarity than that of an inhibition zone (Semi-inhibition zone; translucent zone) and a bacterial zone, which is a region outside thereof and where bacteria are present homogeneously.

Figure 5:
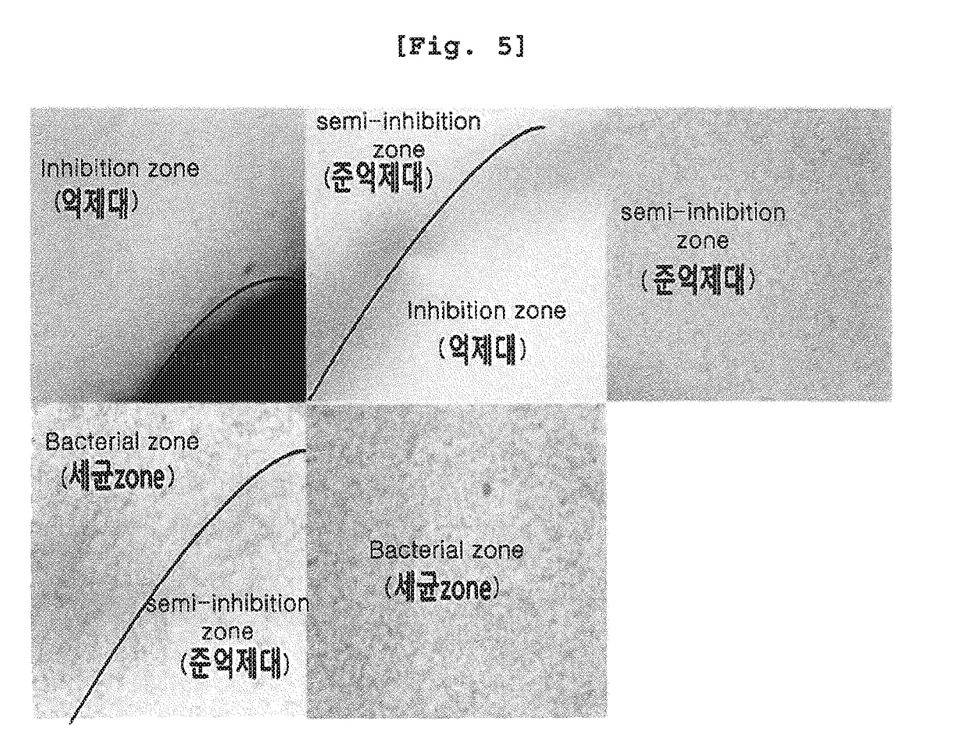
FIG. 5 shows the photographs showing the inhibition zone, the Semi-inhibition zone and the bacterial zone observed with a microscope (500× microscope magnification).
Figure 6:
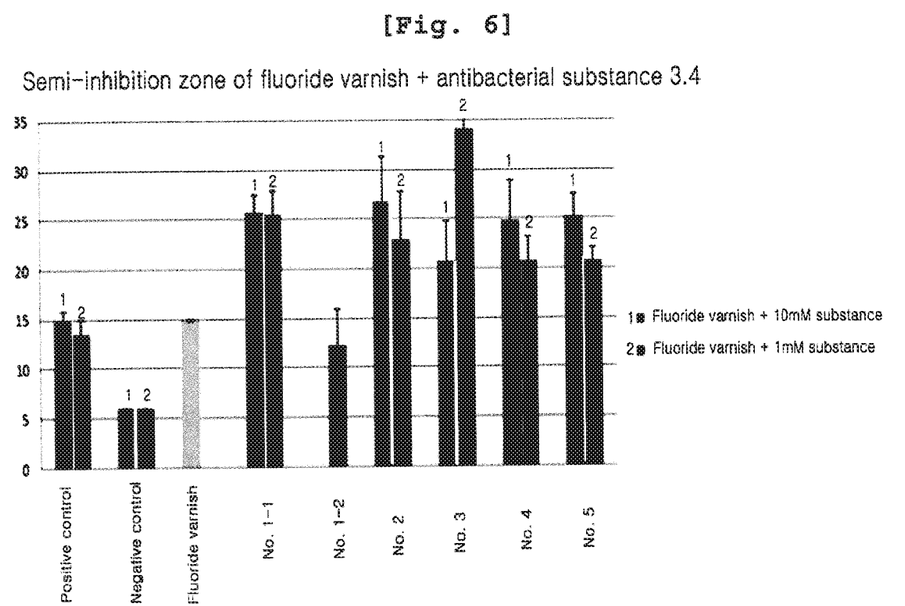
FIG. 6 is a graph showing the results of formation of a Semi-inhibition zone by fluoride varnishes mixed with an antibacterial substance. The terms used are defined as follows.

Specifically, these three zones were observed with a microscope. As shown in FIG. 5, bacteria were present homogeneously in the bacterial zone, no bacteria were present in the inhibition zone, and the Semi-inhibition zone contained a greatly reduced number of bacteria as compared with the bacterial zone.

In addition, the formation of Semi-inhibition zone was investigated according to the same method as in Test Example 1. As shown in the following Table 4 and FIG. 6, the positive control group did not form a Semi-inhibition zone, whereas the fluoride varnish mixed with an antibacterial substance of the present invention formed a large Semi-inhibition zone. In addition, compared with a group treated with a fluoride varnish alone, fluoride varnishes mixed with an antibacterial substance formed a large Semi-inhibition zone. Among the fluoride varnishes mixed with an antibacterial substance, the fluoride varnish mixed with bavachalcone formed the largest Semi-inhibition zone (Table 4 and FIG. 6).

TABLE 4

| Semi-inhibition zone (mm) | Fluoride varnish + 10 mM substance | Fluoride varnish + 1 mM substance | Standard deviation value of fluoride varnish + 10 mM substance | Standard deviation value of fluoride varnish + 1 mM substance |
| --- | --- | --- | --- | --- |
| Positive control group | 15.49 | | 0.58 | |
| Negative control group | 6.00 | | 0 | |
| Fluoride varnish | 14.935 | | 0.091924 | |
| Positive control group | 14.84 | 13.55 | 0.94 | 1.461 |
| Negative control group | 6.00 | 6.00 | 0 | 0.00 |
| No. 1-1 | 25.725 | 25.515 | 1.718269 | 2.439518 |
| No. 1-2 | | 12.265 | 0 | 3.712311 |
| No. 2 | 26.705 | 22.87 | 4.652008 | 4.949747 |
| No. 3 | 20.74 | 34.025 | 4.030509 | 1.138442 |
| No. 4 | 24.81 | 20.795 | 4.101219 | 2.283955 |
| No. 5 | 25.235 | 20.79 | 2.199102 | 1.315219 |

In conclusion, the fluoride varnish mixed with an antibacterial substance according to the present invention showed a similar result to a group treated with an antibacterial substance alone in the formation of an inhibition zone, but brings about a remarkable difference in the formation of a Semi-inhibition zone. Also, a Semi-inhibition zone exhibits antibacterial activities although bacteria are not eradicated as completely as in an inhibition zone. Thus, it was confirmed that a fluoride varnish comprising an antibacterial substance can exhibit significant antibacterial activities in a larger region than a group treated with an antibacterial substance alone.

Test Example 4: Identification of Minimum Inhibitory Concentration (MIC) and Minimal Bactericidal Concentration (MBC)

The minimum inhibitory concentration and minimal bactericidal concentration of antibacterial substances were identified using S. mutans, which is related to dental caries, as the strain.

Specifically, in order to measure MIC, a 96-well plate containing 100 μL of BHI broth per well was used. Antibacterial substances were used at a concentration of 16 mM, and the substance No. 1-2 of Example 1 was used at a concentration of 1 mM. The antibacterial materials were transferred to the first well and diluted stepwise. The substance No. 1-2 was diluted to 1 mM to 0.004375 mM and the other antibacterial substances were diluted to 16 mM to 0.007 mM. S. mutans was activated using BHI broth as the medium and cultured in a $CO_2$ incubator at 37° C. for 24 hours. Then, the bacteria were cultured for another 6 hours, and then 100 μL thereof was added to each well of the 96-well plate. After 24-hour culture, the minimum inhibitory concentration was determined by measuring the absorbance at 600 nm with Enzyme-linked immuno-assay reader (Spectra MAX250, Molecular Devices Co.).

Figure 7:
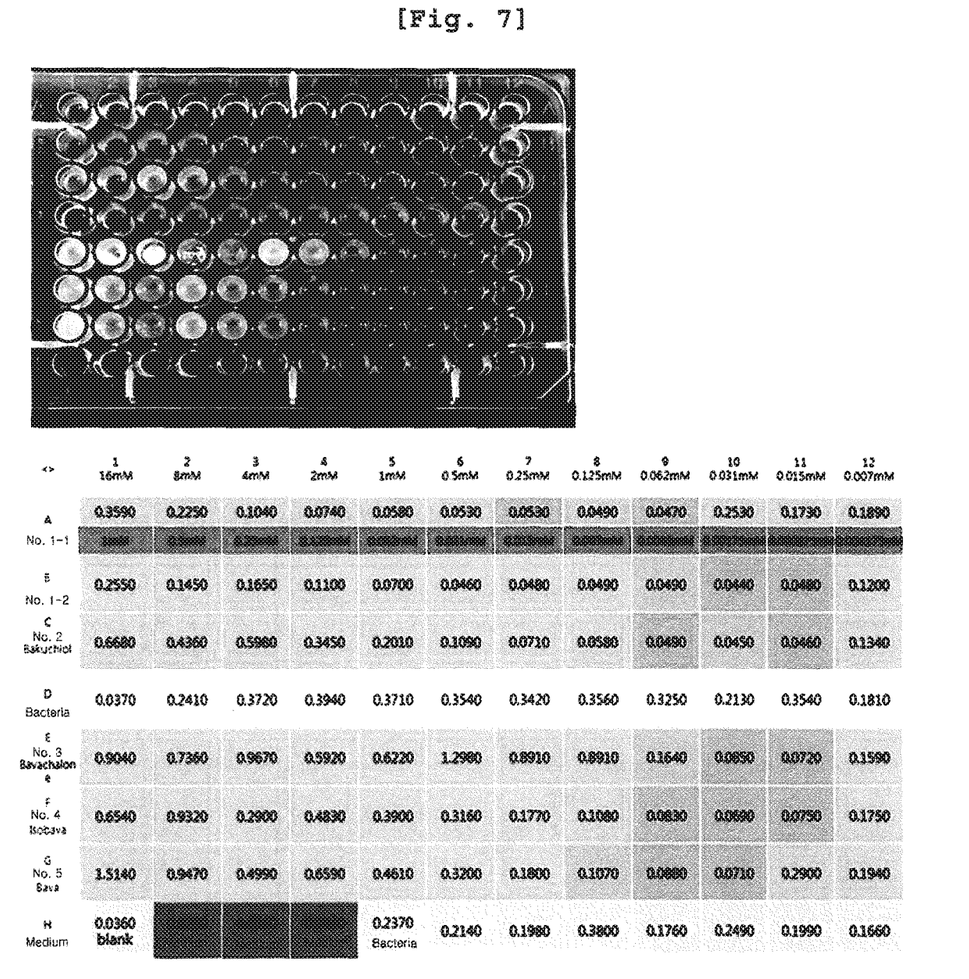
FIG. 7 shows the minimum inhibitory concentration (MIC) and the minimal bactericidal concentration (MBC) of antibacterial substances.

As a result, as shown in the following Table 5 and FIG. 7, it was confirmed that xanthorrhizol (BioAlpha), bakuchiol, bavachalcone and isobavachromene have the lowest MIC, bakuchiol has the lowest MBC, followed by bavachalcone and xanthorrhizol (BioAlpha) (Table 5 and FIG. 7).

TABLE 5

|  | MIC (mM) | MBC (mM) |
|---|---|---|
| xanthorrhizol (Santa Cruz) | 0.062 | 0.125 |
| xanthorrhizol (BioAlpha) | 0.015 | 0.062 |
| bakuchiol | 0.015 | 0.031 |
| bavachalcone | 0.015 | 0.062 |
| isobavachromene | 0.015 | 0.125 |
| bavachromene | 0.031 | 0.125 |

The invention claimed is:

1. A method of treating dental caries comprising administering to a subject afflicted with dental caries a composition comprising a pharmaceutically effective amount of a fluoride varnish and an antibacterial substance as active ingredients, wherein the antibacterial substance is one or more selected from bavachalcone, isobavachromene and bavachromene.

2. The method of claim 1, wherein the fluoride varnish comprises a hydrogenated rosin, a solvent and a fluoride compound.

3. The method of claim 2, wherein the ratio of the hydrogenated rosin, the solvent and the fluoride compound is 30 to 65 wt %: 35 to 65 wt %: 1 to 10 wt %.

4. The method of claim 2, wherein the solvent is one or more selected from distilled water, dimethyl sulfoxide (DMSO), isoamyl propionate, hydrogen fluoride (HF), ethanol, and ethyl acetate.

5. The method of claim 2, wherein the fluoride compound is one or more selected from HF, $NH_4F$, NaF, KF, $Na_2FPO_4$, $K_2FPO_4$, $CaF_2$, $TiF_4$, $Ca_5(PO_4)_3F$, $H_2F_2Si$ (difluorosilane), $C_{16}H_{36}FN$ and $SnF_2$.

6. The method of claim 1, wherein the composition has antibacterial activities against Streptococcus mutans.

7. The method of claim 1, wherein the composition is formulated for use as mouth rinses, teeth desensitizers, antibacterial dental adhesives, dental filling materials, dental restorative materials, dental root canal filling materials, dental root canal sealers, pit and fissure sealants, dental coating materials, or dental cements.

8. A method of treating dental caries comprising administering to a subject afflicted with dental caries a pharmaceutically effective amount of a chalcone-based compound or a pharmaceutically acceptable salt thereof, wherein the chalcone-based compound is any one or more selected from bavachalcone, isobavachromene and bavachromene.

9. The method of claim 8, wherein the chalcone-based compound has antibacterial activities against Streptococcus mutans.

10. The method of claim 8, wherein the chalcone-based compound or pharmaceutically acceptable salt thereof is formulated for use as mouth rinses, teeth desensitizers, antibacterial dental adhesives, dental filling materials, dental restorative materials, dental root canal filling materials, dental root canal sealers, pit and fissure sealants, dental coating materials, or dental cements.

11. The method of claim 8, wherein the chalcone-based compound or pharmaceutically acceptable salt is mixed with fluoride varnish.

* * * * *